United States Patent
McGee

(10) Patent No.: US 11,479,024 B2
(45) Date of Patent: Oct. 25, 2022

(54) MULTILAYER FILMS FOR OSTOMY BAGS

(71) Applicant: TRANSCENDIA, INC., Franklin Park, IL (US)

(72) Inventor: Robert L. McGee, Midland, MI (US)

(73) Assignee: Transcendia, Inc., Franklin Park, IL (US)

( * ) Notice: Subject to any disclaimer, the term of this patent is extended or adjusted under 35 U.S.C. 154(b) by 866 days.

(21) Appl. No.: 16/053,755

(22) Filed: Aug. 2, 2018

(65) Prior Publication Data

US 2019/0039356 A1 Feb. 7, 2019

Related U.S. Application Data

(60) Provisional application No. 62/542,222, filed on Aug. 7, 2017.

(51) Int. Cl.
| | |
|---|---|
| *B32B 27/08* | (2006.01) |
| *A61F 5/441* | (2006.01) |
| *B32B 7/12* | (2006.01) |
| *B32B 27/20* | (2006.01) |
| *B32B 27/22* | (2006.01) |

(Continued)

(52) U.S. Cl.
CPC .............. *B32B 27/08* (2013.01); *A61F 5/441* (2013.01); *B32B 7/12* (2013.01); *B32B 27/20* (2013.01); *B32B 27/22* (2013.01); *B32B 27/304* (2013.01); *B32B 27/306* (2013.01); *B32B 27/32* (2013.01); *B32B 2250/05* (2013.01); *B32B 2250/246* (2013.01); *B32B 2250/40* (2013.01); *B32B 2307/10* (2013.01); *B32B 2307/5825* (2013.01); *B32B 2535/00* (2013.01)

(58) Field of Classification Search
CPC .. A61F 5/44; A61F 5/4401; A61F 5/441–449; B32B 27/08; B32B 27/304; B32B 27/306; B32B 27/32; B32B 27/20; B32B 2250/05; B32B 2250/40; B32B 27/18; B32B 27/22
See application file for complete search history.

(56) References Cited

U.S. PATENT DOCUMENTS

| | | |
|---|---|---|
| 4,687,711 A | 8/1987 | Vietto et al. |
| 5,270,390 A | 12/1993 | Shibuya et al. |

(Continued)

FOREIGN PATENT DOCUMENTS

| | | |
|---|---|---|
| CN | 1365373 A | 8/2002 |
| CN | 1867625 A | 11/2006 |

(Continued)

OTHER PUBLICATIONS

International Search Report and Written Opinion, PCT/US2018/045073, dated Sep. 26, 2018.

(Continued)

*Primary Examiner* — Susan S Su
(74) *Attorney, Agent, or Firm* — Fox Rothschild LLP

(57) ABSTRACT

A multilayer film having at least one barrier layer and at least one outer layer, suitable for medical applications, such as ostomy applications, which is effective as barrier for odors and has sufficient properties with respect to provide a pliable, tear resistant with noise damping film is provided. The multilayer film includes polyolefin elastomers, plasticized PVDC, ethylene vinyl acetate copolymers and additives.

16 Claims, 5 Drawing Sheets

(51) Int. Cl.
  *B32B 27/30* (2006.01)
  *B32B 27/32* (2006.01)

(56) References Cited

U.S. PATENT DOCUMENTS

| | | | |
|---|---|---|---|
| 5,496,295 | A | 3/1996 | Wilfong et al. |
| 5,567,489 | A | 10/1996 | Allen et al. |
| 6,258,423 | B1 | 7/2001 | Glori |
| 6,455,161 | B1 | 9/2002 | Regnier et al. |
| 6,579,584 | B1 * | 6/2003 | Compton ............... B29C 55/28 428/34.6 |
| 6,620,474 | B1 | 9/2003 | Regnier et al. |
| 7,270,860 | B2 | 9/2007 | Glori |
| 9,050,387 | B2 | 1/2015 | Chang et al. |
| 9,283,735 | B2 | 3/2016 | Pham et al. |
| 9,301,869 | B2 | 4/2016 | Chang |
| 2009/0196962 | A1 | 8/2009 | Gkinosatis |
| 2011/0272174 | A1 | 11/2011 | Chaudhary |
| 2013/0096521 | A1 | 4/2013 | Bekele |
| 2014/0221951 | A1 | 8/2014 | Chang |

FOREIGN PATENT DOCUMENTS

| | | |
|---|---|---|
| CN | 102985481 A | 3/2013 |
| CN | 106457754 A | 2/2017 |
| NZ | 567767 A | 5/2010 |
| WO | WO2012/037180 A1 | 3/2012 |
| WO | WO2015/199852 A1 | 12/2015 |

OTHER PUBLICATIONS

Chinese Patent Search Report for Chinese Patent Application No. 2018800516581, dated Jan. 10, 2022, 5 pages.

* cited by examiner

MULTILAYER FILMS FOR OSTOMY BAGS

CROSS-REFERENCE TO RELATED APPLICATION

This application claims the benefit of U.S. Provisional Patent Application No. 62/542,222, filed Aug. 7, 2017, the entirety of which is incorporated by reference herein.

FIELD OF THE INVENTION

The present application discloses a multilayer film, comprising at least one barrier layer and at least one outer layer, suitable for medical applications, such as ostomy applications.

BACKGROUND OF THE INVENTION

Multilayer films containing barriers to odor and moisture are widely used in the medical and food industry fields. As a common medical use, such multilayer barrier films can be used to manufacture ostomy bags or pouches for collecting unpleasant human waste after surgery. An ostomy refers to a surgical procedure which creates an artificial opening in patient to permit the drainage of human waste from the body, such as colostomy, ileostomy, and urostomy. Human waste contains various compounds with different molecular sizes. Ostomy pouches desirably should have certain characteristics to meet medical and social needs, including impermeability to odor compounds and water to prevent the release of unpleasant odors of the human waste, stability under dry and moisture conditions, a tough structure having a high tensile strength and elasticity to prevent tearing, softness and low toxicity to prevent damage to patients' skin for patients and to provide comfortable wear, and damping properties to absorb noise to avoid embarrassment of the wearer.

The release of body waste and the emission of intestinal gas may cause a transitional vibration in the body tissues accompanied by noisy sound with malodor. It is desirable that the films for manufacturing ostomy pouches have noise damping properties to absorb sound. In addition, an ostomy pouch with a quiet film which has relatively low plastic crackling noise when the ostomy pouch is flexed or wrinkled is preferred to help avoid embarrassment of the wearer. Therefore, typically multilayer films used for making ostomy pouches comprise at least one barrier layer and at least one outer layer to provide the desired characteristics.

The film used for ostomy applications commonly has a multilayer structure which comprises at least one outer layer as a layer contacting patients' skin or as a surface protective layer, at least one barrier layer to prevent small molecules from penetrating the film, tie layers as adhesive layers to contact and join the layers together, and other intermediate layers as needed. In general, the layers contact and locate immediately adjacent to the barrier layer are tie layers functioned as adhesive layers. The outer layer serves as the cling component and the surface protective film in multilayer stretch film.

The thicknesses and compositions of each individual layer and the overall multilayer structure will depend on various factors pertained to the multilayer films, which are adaptive to the intended applications, convenience and cost of manufacturing, specific physical and chemical properties, and the environment to which the multilayer films will be exposed. Commonly, the thickness of the multilayer film is in the range of from 20 μm to 350 μm, but the compositions of the polymeric layers are variable.

Conventionally, multilayer films for ostomy applications utilize polyvinylidene chloride (PVDC) or copolymers of vinylidene chloride with a copolymonomer such as methylacrylate or vinylchloride as the gas barrier layer. Low density polyethylene (LDPE), polyvinyl chloride (PVC), or chlorinated polyethylene (CPE) blended with ethylene-vinyl acetate (EVA) copolymer can be used as the structural and sealant layer. Such multilayer films have resistance to odor transmission and are not adversely affected by the presence of moisture.

Various compositions and multilayer structures have been disclosed to construct multilayer films for relevant applications with desired characteristics, such as for ostomy uses. Regnier et al. (U.S. Pat. No. 6,620,474 B1) discloses essentially amorphous (low-crystallinity), non-chlorinated polymeric films as effective barriers to odors and organic molecules, discloses the use of at least one polymer layer having noise dampening properties, and discloses the use of copolymers of olefins and polar co-monomers additionally to improve the high frequency sealing properties of the film. It also discloses the uses of chlorinated polymers optionally with the essentially amorphous, non-chlorine containing barrier films, such as polyvinyl chloride (PVC), chlorinated polyethylene (CPE), polyvinylidene chloride (PVDC), PVDC/VC copolymers (PVDC/VC), PVDC/methyl acrylate copolymers (PVDC/MA), and mixtures thereof.

Vietto et al. (U.S. Pat. No. 4,687,711) discloses quiet and pliable films which comprise at least one layer formed from a polymeric blend including copolymers of ethylene and vinyl-acetate and an elastomeric polyolefin for manufacturing drainage containers or bags for medical applications. Giori (U.S. Pat. No. 7,270,860 B2) discloses a multilayer heat-sealable chlorine-free film comprising an odor barrier layer of an amorphous polyamide resin blended with an anhydride-modified olefinic polymer or copolymer. The multilayer films made of such amorphous polyamine modified with a functionalized polyolefin have reduced rigidity with less plastic crackling noise when compared to non-modified amorphous polyamine.

Chang et al. (U.S. Pat. No. 9,301,869 B2) describes a multilayer film comprising a barrier layer formed from a non-chlorine containing amorphous polyamide resin and a maleic anhydride modified olefin or an epoxy modified olefin, tie layers made of a maleic anhydride grafted resin, inner layers made of an ethylene propylene copolymer based resin, and an outer layer made of an ethylene vinyl acetate or ethylene methyl acrylate copolymer or a blend thereof.

Commonly the elastomer used in preparing the polymer for constructing the outer layer of the multilayer film is chlorinated polyethylene (CPE) which leads to a derived copolymer based on high density polyethylene. When the ostomy pouch is made of such copolymer, it has relatively poor tear strength, and that can lead to the failure of the ostomy pouch prior to end use. Thus, improvements in such pouch materials is needed and these are now provided by the present application.

SUMMARY OF THE INVENTION

An approach of the present inventive concept utilizes a polyolefin elastomer such as an ethylene-octene copolymer as the polymer of the outer layer to enhance tear performance of the multilayer film. In addition, conventional barrier layers can be provided although preferably, the barrier layer is plasticized polyvinylidene chloride (PVDC) copolymer to effectively prevent the release of unpleasant odors of human waste. The present application provides a multilayer film that is particularly useful for medical use, such as an ostomy application, due to its exceptional properties as an odor barrier and being tear resistant while at the same time being soft to touch with low modulus and low noise generation.

In accordance with principles of the present application, a multilayer film is provided for medical applications, such as for use in ostomy applications. The multilayer film comprises: an outer layer as a surface protective layer, the outer layer made of a polymer comprising a polyolefin elastomer, a plasticizer of an epoxidized vegetable oil, and a mineral filler; and a barrier layer for preventing the transmission of small molecules from penetrating the multilayer film; wherein the layers of the film are joined together by an adhesive. In some embodiments, the outer layer further comprising an ethylene-vinyl acetate (EVA) copolymer, the adhesive is provided in a tie layer that contacts and joins the barrier layer and the outer layer together, and the barrier layer is made of a polymer comprising a polyvinylidene chloride (PVDC) that is plasticized by an epoxidized vegetable oil.

In one embodiment, a multilayer film for ostomy application has a total thickness of from 45 micron to 85 micron and comprises four layers in the sequence of that a first layer is the outer layer, a second layer is the first tie layer, a third layer is the barrier layer, and a fourth layer is the second tie layer, wherein a thickness of the outer layer (such as comprising a polyolefin elastomer) is from 30% to 70% (preferred at 49%) of the total thickness of the multilayer film, a thickness of a first tie layer is from 6% to 12% (preferred at 9%) of the total thickness of the multilayer film, a thickness of the barrier layer (such as comprising PVDC) is from 4% to 10% (preferred at 5%) of the total thickness of the multilayer film, and a thickness of a second tie layer is from 30% to 45% (preferred at 37%) of the total thickness of the multilayer film.

A multilayer film for ostomy application comprises at least one tie layer and at least one barrier layer, wherein the tie layer may be located adjacent to the barrier layer. The tie layer glue layer or adhesive layer) may be provided adjacent to the outer layer or the barrier layer to facilitate the adhesion between layers within the multilayer structure. In the embodiment of FIG. 1, a tie layer 40 is arranged between an outer layer 30 and a barrier layer 50, and a tie layer 41 is arranged adjacent to a barrier layer 50. The tie layer 40 and 41 may be made of a same material or different materials depending on the compositions of the adjacent layers.

In another aspect, the multilayer films for ostomy application may include an additional enhanced-polymer layer to provide additional mechanical properties with improved tear strength, such as an enhanced-polymer layer comprising polyethylene polymer. In one embodiment, a multilayer film for ostomy application may further comprise two enhanced-polymer layers, wherein a first enhanced-polymer layer and a second enhanced-polymer layer comprise polyethylene polymer, and wherein the barrier layer is located between the first enhanced-polymer layer and the second enhanced-polymer layer. The polyethylene polymer of the embodiment may comprise a linear low density polyethylene polymer.

In one embodiment, a multilayer film for ostomy application comprises five layers in the sequence of that the first layer is the outer layer, a second layer is a first tie layer, a third layer is the barrier layer, a fourth layer is a second tie layer, and a fifth layer is the outer layer. In one embodiment, a multilayer film for ostomy application comprises seven layers in the sequence of that a first layer is the outer layer, a second layer is the first tie layer, a third layer is a first enhanced-polymer layer, a fourth layer is the barrier layer, a fifth layer is a second enhanced-polymer layer, a sixth layer is a second tie layer, and a seventh layer is the outer layer.

In some embodiments, a product such as an ostomy bag is made of the multilayer film of the present application for ostomy application; wherein the outer layer is made of an outer layer mixture, wherein the polyolefin elastomer is present in an amount of from 20 wt % to 90 wt % of the outer layer mixture, the epoxidized vegetable oil is an epoxidized soybean oil, and the mineral filler is talc; wherein the barrier layer comprises a polymer comprising a polyvinylidene chloride that is plasticized by an epoxidized soybean oil.

BRIEF DESCRIPTION OF THE FIGURES

Further features of the inventive concept, its nature and various advantages will be more apparent from the following detailed description, taken in conjunction with the accompanying drawings in which like reference characters refer to like parts throughout and in which.

DETAILED DESCRIPTION

Figure 1:
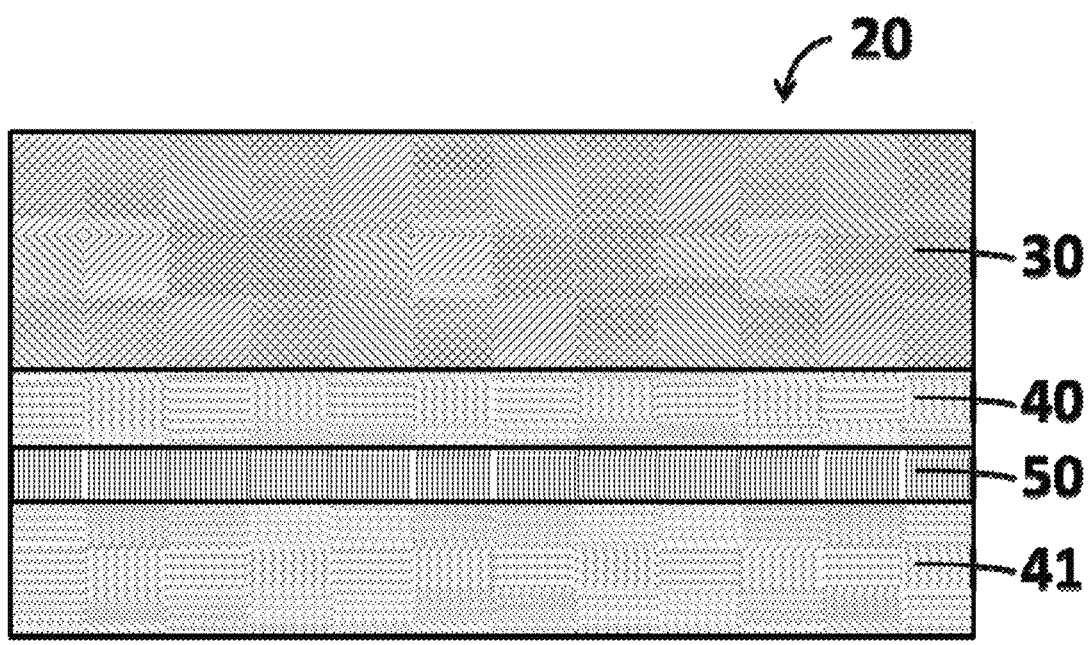
FIG. 1 is a cross-sectional illustration of a multilayer film comprising four-layer film (20) contains an outer layer (30), a first tie layer (40), a barrier layer (50) and a second tie layer (41) according to an embodiment of the present application.

Throughout this description, the preferred embodiments and examples provided herein should be considered as exemplar, rather than as limitations of the present application.

Certain terms that are used herein are defined herein below to assist in the understanding of the present application. The term "Elmendorf tear strength" is used to indicate the tearing resistance properties of the films prepared in this application by measuring the force required to propagate the tearing of a film for a predetermined distance by measuring the loss of potential energy from a pendulum. All ranges recited herein are approximate and can vary by as much as ±10% to in some cases±25%. In some situations, the term "about" is used to indicate this tolerance. And when the term "about" is used before reciting a range, it is understood that the term is applicable to each recited value in the range.

The multilayer film of the present application is pliable with low noise generation and provides good tear resistance, which are useful in ostomy applications with superior performance over conventional film. The multilayer film of the present application is particularly useful for ostomy bags (colostomy, ileostomy), trans-dermal delivery systems (TDDS), cosmetic patches, incontinence bags, medical collection bags, and parenteral solution bags.

The polymer of the outer layer of the multilayer film of the present application, which is chlorine-free and essentially semi-crystalline and unexpectedly has low noise generation properties, comprises polyolefin elastomer compound (such as ethylene-octene based elastomers) containing epoxidized soybean oil (ESO) and talc, ethylene-vinyl acetate (EVA) copolymer, and additives. In addition, epoxidized soybean oil (ESO) plasticized polyvinylidene chloride (PVDC) copolymers are used as a barrier layer to effectively prevent the release of unpleasant odors of human wastes. The outer layer is coupled with plasticized PVDC copolymers in multilayer structures to provide exceptional performance. The multilayer film of the present application is effective in preventing the release of unpleasant odor and has stability under moisture conditions, improved toughness with high tensile strength to prevent tearing, softness and pliableness with low modulus, and low noise generation.

In at least some embodiments, the outer layer of the multilayer film is made with a polyolefin elastomer, preferably an ethylene-octene elastomer with density less than 0.91 g/cc, to enhance tear performance of the multilayer film. In one embodiment, the multilayer film comprises a barrier layer which comprises a polyvinylidene chloride (PVDC) that is plasticized by an epoxidized soybean oil in the range of less than 3%. In one embodiment, an ostomy pouch is made of any of the multilayer film of the present application, wherein the multilayer film includes a first wall and a second wall, wherein the first wall and the second wall are sealed along their peripheral edges to define a cavity, wherein the outer layer may be a seal layer.

The multilayer films of the present application have an Elmendorf tear strength in the machine direction measured by ASTM D1922-09 of at least about 100 grams/25.4 microns. The multilayer films of the present application have a tensile modulus at 1% Secant Modulus (measured according to ASTM D-882) of less than 80 MPa, preferably less than 70 MPa.

In some preferred embodiments, the multilayer film of the present application comprises an outer layer, a first tie layer, a barrier layer, and a second tie layer:

The outer layer comprises:

(a). a polyolefin elastomer (such as ENGAGE™, an ethylene-octene elastomer) with the addition of an epoxidized vegetable oil (such as epoxidized soybean oil) as a plasticizer, and with the addition of a mineral filler (such as talc), wherein the outer layer is made of an outer layer mixture, wherein the polyolefin elastomer is in the range of from 20 wt % to 90 wt % of the outer layer mixture (preferred at 62 wt %), wherein the epoxidized soybean oil is in the range of from 0.5 wt % to 6.0 wt % of the outer layer mixture, wherein the talc is in the range of from 0.5 wt % to 6.0 wt % of the outer layer mixture, wherein the polyolefin elastomer, the epoxidized vegetable oil, the mineral filler, and other additional components present in a total amount of 100% of the outer layer mixture.

A preferred embodiment used 80 wt % (in the weight of the outer layer mixture) of a formulation comprising ENGAGE™ 8100 at 39 wt %, ENGAGE™ 8200 at 39 wt %, Elvax® 3150A at 17.55 wt %, talc at 3.2 wt % and epoxidized soybean oil at 1.25 wt %.

(b). 15 wt % to 40 wt % (in the weight of the outer layer mixture) (preferred at 26 wt %) of a 12-24 wt % (preferred at 15 wt %) of vinyl acetate comonomer (an ethylene-vinyl acetate copolymer resin)

A preferred embodiment used a 26 wt % (in the weight of the outer layer mixture) of a formulation comprising 26 wt % of Elvax® 3150 (an ethylene-vinyl acetate copolymer resin contains 15% vinyl acetate comonomer).

(c). 1 wt % to 6 wt, 0 (in the weight of the outer layer mixture) (preferred at 3 wt %) of a slip/antiblock composition, such as a composition comprising 4 wt % octadecanamide, 4 wt % erucamide, and 8 wt % calcined silica in balance of ethylene-vinyl acetate copolymer slip/antiblock compound.

A preferred embodiment used a 3 wt % (in the weight of the outer layer mixture) of a formulation comprising CN-4420 (a slip/antiblock additive).

(d). 1 wt % (in the weight of the outer layer mixture) of a process aid composition, such as a fluoroelastomer in polyethylene.

A preferred embodiment used 1 wt % (in the weight of the outer layer mixture) of a formulation comprising Ampacet 102113 (a process aid additive).

In one aspect, a multilayer film for ostomy application comprises a tie layer, wherein the tie layer is made of a tie layer mixture, wherein the tie layer mixture comprises 50 wt % to 90 wt % (in the weight of the tie layer mixture) (preferred at 70 wt %) of a 24% vinyl acetate copolymer (such as EVATANEÂ® 24-03 purchased from Arkema Group, which is a random copolymer of ethylene and vinyl acetate and contains 24% of vinyl acetate), 10 wt % to 50 wt % (in the weight of the tie layer mixture) (preferred at 20%) of a 18% vinyl acetate copolymer (such as Elvax® 3165LG purchased from DuPont Company, which is an extrudable ethylene-vinyl acetate copolymer resin at density of 0.94 g/cm$^3$ and contains 18 wt % vinyl acetate comonomer), 5 wt % to 15 wt % (in the weight of the tie layer mixture) (Preferred at 10 wt %) of a composition comprising slips, antiblocks and process aids, wherein the vinyl acetate copolymers, slips, antiblocks, process aids, and other additional components are present in a total amount of 100% of the tie layer mixture.

In some preferred embodiments, the barrier layer is a plasticized polyvinylidene chloride (PVDC). A preferred embodiment used 100 wt % of SARAN™ XUS 32727.00 (PVDC) as the barrier layer.

EXAMPLE

It is to be understood that the presently disclosed inventive concept is not to be limited to the exact description and embodiments as illustrated and described herein. To those of ordinary skill in the art, one or more inventive concepts will be understood to be contemplated from the present application. Accordingly, all expedient modifications readily attainable by one of ordinary skill in the art from the disclosure set forth herein, or by routine experimentation there from, are deemed to be within the spirit and scope of the present application as defined by the appended claims.

Several multilayer films for ostomy application at different thicknesses, such as at the thickness of 65 or 75 microns, were prepared. The following are examples of multilayer films which were tested for stiffness, tear strength, strain, toughness, softness or noise intensity. Conventional processes such as blowing or casting, co-extrusion, extrusion coating, extrusion lamination, or adhesive lamination may prepare the multilayer film structures of the present inventive concept.

Materials:

Ampacet 101830 (antiblock PE MB_RM) is purchased from Ampacet Corporation and contains 50% silicate (nepheline syenite) in LDPE and LLDPE at Melt Index at 190° C./2.16 kg per 10 min.

Ampacet 101830-U (antiblock PE MB_RM) is purchased from Ampacet Corporation and contains 50% aluminosilicate in LDPE and LLDPE.

Ampacet 102113 Process Aid contains a vinylidene fluoride hexafluoropropylene copolymer in LLDPE (2% Viton Free Flow Z200), which is purchased from Ampacet Corporation.

CN-707A is an EVA-based slip concentrate and contains 10 wt % erucamide in EVA.

CN-745 compound is a chlorinated polyethylene concentrate and contains TYRIN™ 361 at 76.7%, Elvax® 3150 at 17.5%, talc at 3.25%, epoxidized soybean oil at 1.25%, and calcium stearate at 1.3%.

CN-4420 compound is a slip/antiblock concentrate and contains 4% stearamide, 4% erucamide and 20% slip/antiblock ($SiO_2$ in Elvax® 3174 EVA 18% VA).

Elvax® 3150 (purchased from DuPont Company) is an extrudable ethylene-vinyl acetate (EVA) copolymer resin (density at 0.94 $g/cm^3$, Melt Flow Rate at 2.5 g/10 min, melting point at 92° C., freezing point at 71° C., and vicat softening point at 66° C.) and contains 15 wt % vinyl acetate comonomer for the use of processing polyethylene resins in extrusion equipment.

Elvax® 3150A (purchased from DuPont Company) is an extrudable ethylene-vinyl acetate (EVA) copolymer resin (density at 0.94 $g/cm^3$, Melt Flow Rate at 2.5 g/10 min, melting point at 91° C., freezing point at 74° C., and vicat softening point at 66° C.) and contains 15 wt % vinyl acetate comonomer for the use of processing polyethylene resins in extrusion equipment.

Elvax® 3165LG (purchased from DuPont Company) is an extrudable ethylene-vinyl acetate copolymer resin at density of 0.94 $g/cm^3$ and Melt Flow Rate of 0.7 g/10 min and contains 18 wt % vinyl acetate comonomer.

Elvax® CE9619-1 (purchased from DuPont Company) is an extrudable ethylene-vinyl acetate copolymer resin concentrate and contains 73 wt % of an 18 wt % vinyl acetate comonomer content resin, 20 wt % inorganic antiblock agent, and 7 wt % amide based slip agent.

ENGAGE™ 8100 and ENGAGE™ 8200 were purchased from The Dow Chemical Company. ENGAGE™ 8100 is a polyolefin elastomer (an ethylene/1-octene elastomer) which has 0.75-1.25 dg/min Melt Index at 190° C./2.16 kg measured by ASTM D1238 and 0.8670-0.8730 $g/cm^3$ density measured by ASTM D792. ENGAGE™ 8200 is a polyolefin elastomer (an ethylene/1-octene elastomer) which has 4.0-6.0 dg/min Melt Index at 190° C./2.16 kg measured by ASTM D1238 and 0.8670-0.8730 $g/cm^3$ density measured by ASTM D792. Epoxidized soybean oil and talc were added either to ENGAGED' or EVA as plasticizers by a commercial company, e.g. a compounder.

Escorene™ FL 00623 (purchased from ExxonMobil) is an ethylene vinyl acetate copolymer resin at 23 wt % vinyl acetate content at Melt Index of 5.5 g/10 min and density of 0.947 $g/cm^3$.

EVATANE® 24-03 is a random copolymer of ethylene and vinyl acetate and contains 24% vinyl acetate with 3 Melt Index g/10 min. It was purchased from Arkema Group.

SARANEX™ 635G is a commercial grade ostomy film made by Transcendia. It is a four-layer coextruded film with low noise, which was designed for ostomy and other medical applications.

SARAN™ XUS 32727.00 Developmental MA Barrier Polymer is purchased from The Dow Chemical Company and contains a vinylidene chloride/methyl acrylate copolymer with less than 3 wt % epoxidized soybean oil. SARAN™ XUS 32727.00 was provided as a PVDC (polyvinylidene chloride) barrier layer in experimental multilayer films of the present application.

TYRIN™ 3611E resin (purchased from The Dow Chemical Company) is a low viscosity chlorinated polyethelene with low crystallinity at density of 1.17 $g/cm^3$ and chlorine content of 36 wt %. TYRIN™ 3611E resin is used for polymer modification in various products, such as film.

Methods

Noise Intensity Measurement

A $10 \times 10$ $cm^2$ size sample is cut in the multilayer film with the machine (MD) and transverse direction (TD) parallel to the sides of the sample. The film sample is adhered to two circular holders with a diameter of 32 mm using double side adhesive tapes. These two circular holders are 90 mm apart from each other. The sample film has the shape of a vertical cylinder (with a diameter of 32 mm) with one slit along its axis. The machine direction (MD) of the film sample is parallel to the axis of the cylinder. Any folds in the cylindrical film sample are eliminated. The bottom circular holder is stationary, while the upper holder is connected to an alternating drive mechanism.

A microphone is placed at 17 mm from the edge at half height of the film cylinder and at 90° angle from the slit. The microphone is connected to a noise analyzer having an octave frequency filter (Bruel & Kjaer Model 2250 Hand-Held Analyzer). The noise analyzer is set in "P" (peak) mode at range 2. The entire assembly is enclosed in a polyurethane foam lined sound insulated box with the exception of the motor of the drive unit and the noise meter. The internal dimensions of the box are X cm×Y cm×Z cm (length× width×height).

After starting the motor, the film sample makes an alternative flexing motion in 60° angel at the flexing frequency of 0.6 Hz. The noise made by the flexing motion of the film sample in the octave frequency bands from 16 Hz to 16 kHz is recorded in the decibel A scale [dBA]. Two to four measurements are made with the calculation of an average for each frequency band. The tests are conducted at ambient temperature (approximately 23° C.). The results of noise intensity are averaged at 1, 2, 4, 8, and 16 KHz.

Sensory Testing

A sensory panel study with 24-35 panelists is conducted to evaluate the perception of the haptic characteristics of different multilayer film by ranking the attributes of softness, stiffness and noise intensity in the scale of 1-5. The scale of 1 is defined as "not soft", "stiff", or "loud" for each attribute respectively. The scale of 5 is defined as "soft", "pliable", or "quiet" for each attribute respectively. Each attribute is analyzed using an F-statistic in Analysis of Variance (ANOVA) to determine if there are any significant differences among the samples in the multiple comparisons. The F-ratio in the ANOVA indicates significant differences among samples. A Fisher's Least Significant Difference (LSD) is calculated to determine One-at-a-Time multiple comparisons. The Fisher's LSD test is used for pairwise comparisons, when a significant F-value has been obtained.

Example 1. The Comparison of Chlorinated Polyethelene (CPE) and e Ylene-Octene Elastomer in Outer Layer of the Multilayer Film Several multilayer films at the thickness of 65 or 75 micron were prepared and tested for sensory testing, noise generation testing (noise intensity measurement), tensile properties, and Elmendorf tear properties. The multilayer film contained chlorinated polyethelene (CN-745 compound containing Tyrin 3611E at 76.7%, Elvax 3150 at 17.5%, talc at 3.25%, epoxidized soybean oil at 1.25%, and calcium stearate at 1.3%) in outer layer was used as control to compare with the experimental multilayer film contained an ethylene-octene elastomer in outer layer. The multilayer films were provided in SARANEX™ 635G Clear Light Embossed quiet film formulation as the base film formulation. In the experimental multilayer film, CN-745 compound was replaced by ethylene-octene elastomer, e.g. ENGAGE™ compound containing epoxidized soybean oil and talc.

The layers of the multilayer films were joined together and contacted each other in the sequence as outer layer, tie layer 1, barrier layer, and tie layer 2 (as glue layer). The layer profile targets of the multilayer films are described in table 1. The compositions of the outer layers are described in table 2. The tie layer comprised Escorene™ FL 00623 at 92.5 wt %, Elvax® CE9619-1 at 5.5 wt %, Ampacet 101830 at 1 wt %, and Ampacet 102113 at 1%. The barrier layer contains 100% SARAN™ XUS 32727.00 (PVDC).

TABLE 1

The layer profile targets of the multilayer films

| Film No. | 886868 | 886869 | 886870 | 886871 | 886872 |
|---|---|---|---|---|---|
| Thickness of film | 75 microns | 75 microns | 75 microns | 65 microns | 65 microns |
| Outer, layer profile target | 48.8% | 48.8% | 48.8% | 48.8% | 48.8% |
| Tie-1, layer profile target | 9.3% | 9.3% | 9.3% | 9.3% | 9.3% |
| Barrier, layer profile target | 8.5% | 8.5% | 5.4% | 5.4% | 5.4% |
| Tie-2, layer profile target | 33.4% | 33.4% | 36.5% | 36.5% | 36.5% |

ENGAGE™ mixture, e.g. the ethylene-octene elastomer, used in the experimental multilayer films in table 2 was a 50/50 blend of ENGAGE™ 8100 and ENGAGE™ 8200 at the composition of ENGAGE™ 8100 at 39 wt %, ENGAGE™ 8200 at 39 wt %, Elvax® 3150A at 17.55 wt %, talc at 3.2 wt % and epoxidized soybean oil at 1.25 wt %

TABLE 2

The compositions of the outer layer of the multilayer films.

| | Film No. | | | | |
|---|---|---|---|---|---|
| | 886868 wt % | 886869 wt % | 886870 wt % | 886871 wt % | 886872 wt % |
| CN-745 (CPE) | 80 | NA | NA | NA | NA |
| ENGAGE ™ mixture (ethylene-octene elastomer) | NA | 81 | 81 | 81 | 70.5 |
| Elvax ® 3150A (EVA) | 15.5 | 15.5 | 15.5 | 15.5 | 26 |
| CN-707A (slip antiblock, EVA based) | 3.5 | 2.5 | 2.5 | 2.5 | 2.5 |
| Ampacet 102113 (process aid additive) | 1 | 1 | 1 | 1 | 1 |

ENGAGE™ mixture is a 50/50 blend of ENGAGE™ 8100 and ENGAGE™ 8200 at the composition of ENGAGE™ 8100 at 39 wt %, ENGAGE™ 8200 at 39 wt %, Elvax® 3150A at 17.55 wt %, talc at 3.2 wt % and epoxidized soybean oil at 1.25 wt %.

Figure 2:
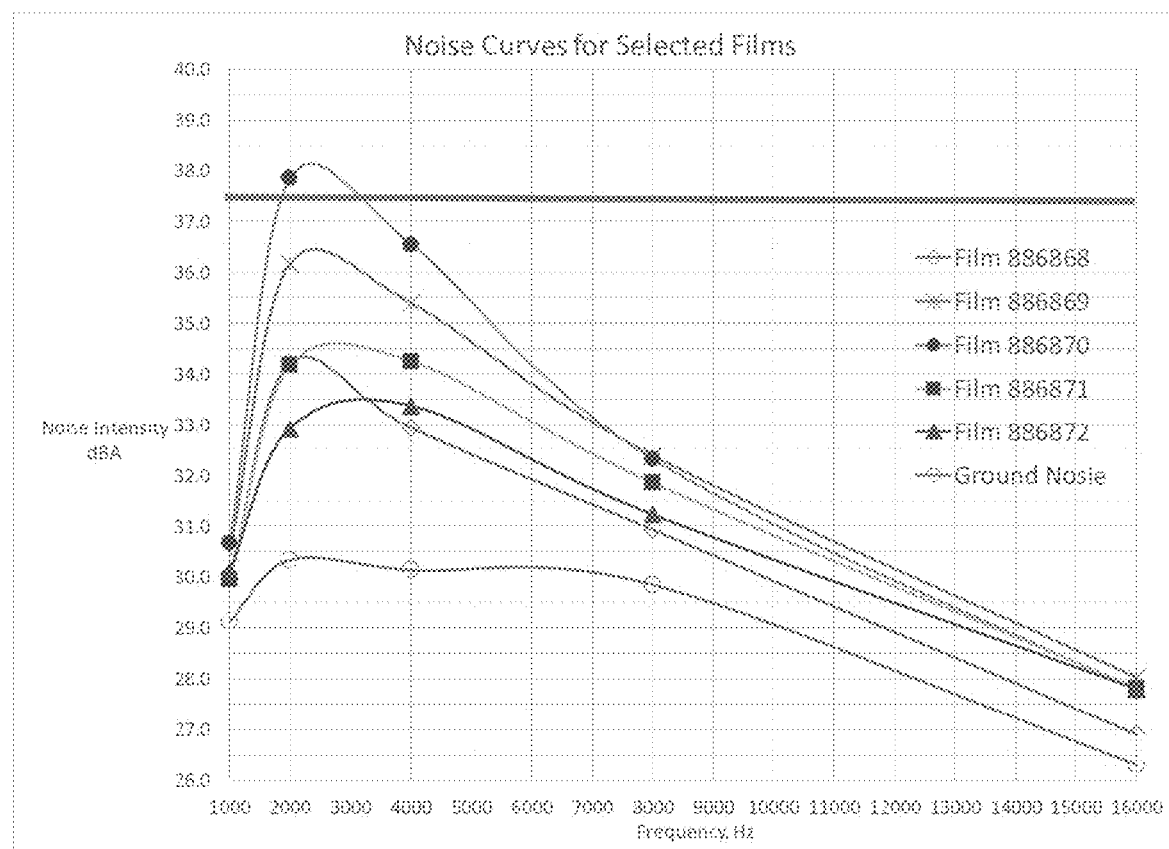
FIG. 2 is a diagram showing noise curves of multilayer films.

The control and experimental multilayer films were tested for noise generation, e.g. noise intensity measurement. All of the experimental multilayer films (film no. 886869, 886870, 886871, and 886872) had comparable performances as quiet films in the tests of noise generation compared to the control multilayer film (film no. 886868). For noise intensity measurement, the differences of about 3 to 5 dBA or less are not detectable by human ear. As shown in table 3 and FIG. 2, none of the average values of the noise intensities of the experimental multilayer films in the range of 1000 to 16000 Hz showed differences compared to the control multilayer film by more than about 2.5 dBA.

TABLE 3

Noise intensity in dBA for different octave frequency bands.

| Film No. | 1 kHz | 2 kHz | 4 kHz | 8 kHz | 16 kHz | Average dBA | Std Dev dBA |
|---|---|---|---|---|---|---|---|
| 886868 | 29.9 | 34.2 | 32.9 | 30.9 | 26.9 | 31.0 | 2.8 |
| 886869 | 30.5 | 36.2 | 35.4 | 32.4 | 28.0 | 32.5 | 3.4 |
| 886870 | 30.7 | 37.9 | 36.5 | 32.3 | 27.8 | 33.0 | 4.2 |
| 886871 | 30.0 | 34.2 | 34.3 | 31.9 | 27.8 | 31.6 | 2.8 |
| 886872 | 30.1 | 32.9 | 33.4 | 31.2 | 27.8 | 31.1 | 2.3 |
| Ground noise | 29.1 | 30.3 | 30.1 | 29.9 | 26.3 | 29.2 | 1.7 |

Figure 3:
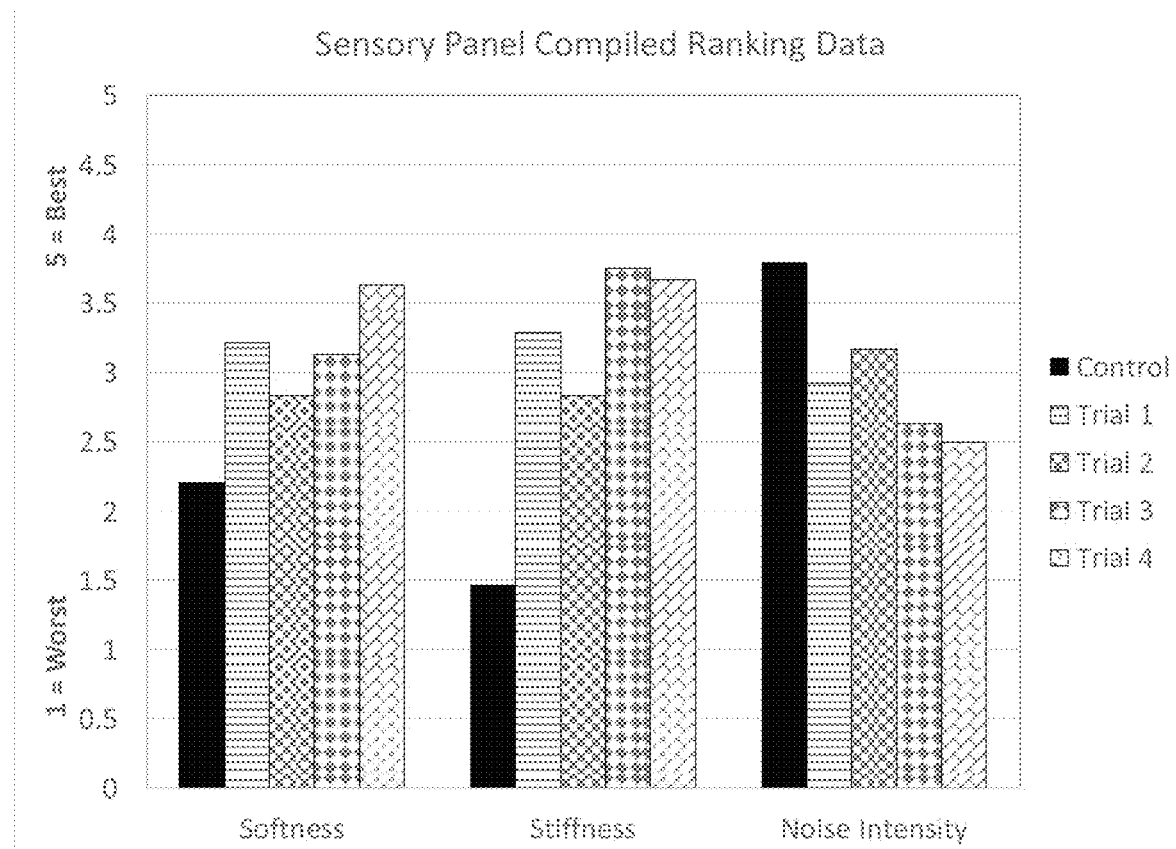
FIG. 3 is a diagram showing the testing results of a sensory panel study which was conducted to evaluate the perception of the haptic characteristics of different multilayer films by ranking the attributes of softness, stiffness and noise intensity in the scale of 1-5. The scale of 5 is defined as "soft", "pliable", or "quiet" for each attribute respectively. The control multilayer film was film no. 886868. The experimental films were in trial 1-4. Trial 1 was film no. 886869; trial 2 was film no. 886870; trial 3 was film no. 886871; and trial 4 was film no. 886872.

A sensory panel study with panelists was conducted to evaluate the perception of the haptic characteristics of different multilayer films by ranking the attributes of softness, stiffness and noise intensity in the scale of 1-5. The scale of 5 is defined as "soft", "pliable", or "quiet". As shown in FIG. 3, all of the experimental multilayer films (film no. 886869, 886870, 886871, and 886872) had good performances in ranking the attributes of softness and stiffness as being soft and pliable compared to the control multilayer film (film no. 886868).

The test results of tensile properties and Secant Modulus of the control and experimental multilayer films, which were measured according to ASTM D-882, are shown in tables 4 and 5. The experimental multilayer films (film no. 886869, 886870, 886871, and 886872) had the values of tensile modulus at 1% Secant Modulus at less than 80 MPa, preferably less than 70 while the control multilayer film (film no. 886868) had the values of tensile modulus at 1% Secant Modulus at 97.2 MPa in MD and 101.4 MPa in CD.

TABLE 4

Tensile properties per ASTM D-882

| | 886868 | 886869 | 886870 | 886871 | 886872 |
|---|---|---|---|---|---|
| Thickness, MD (μm) | 73.3 | 71.2 | 78.2 | 65.2 | 65.4 |
| Std Dev (μm) | 1.1 | 2.9 | 1.2 | 3.3 | 1.9 |
| Stress at break, MD (MPa) | 17.9 | 16.3 | 16.9 | 17.4 | 18.1 |
| Std Dev | 0.6 | 0.81 | 0.6 | 1.0 | 0.8 |
| Strain at break, MD (%) | 393 | 390 | 437 | 400 | 403 |
| Std Dev | 10 | 19 | 6 | 13 | 16 |
| Toughness, MD (MPa) | 36.2 | 34.1 | 38.2 | 36.6 | 38.5 |
| Std Dev | 1.6 | 2.6 | 1.3 | 2.8 | 2.5 |
| Thickness, CD (μm) | 72.3 | 71.2 | 74.2 | 64.8 | 65.4 |
| Std Dev (μm) | 0.8 | 1.8 | 0.6 | 2.0 | 0.8 |
| Stress at break, CD (MPa) | 13 | 11.7 | 11.9 | 11.4 | 11.7 |
| Std Dev | 0.6 | 0.2 | 0.2 | 0.2 | 0.2 |
| Strain at break, CD (%) | 506 | 525 | 571 | 537 | 537 |
| Std Dev | 19 | 21 | 12 | 11 | 16 |

TABLE 4-continued

Tensile properties per ASTM D-882

|  | 886868 | 886869 | 886870 | 886871 | 886872 |
|---|---|---|---|---|---|
| Toughness, CD (MPa) | 31.7 | 31.4 | 35.3 | 30.6 | 31.4 |
| Std Dev | 2.2 | 1.7 | 1.3 | 1.1 | 1.6 |

TABLE 5

Secant Modulus per ASTM D-882 (in MPa)

|  | 886868 | 886869 | 886870 | 886871 | 886872 |
|---|---|---|---|---|---|
| 1% Secant Modulus, MD Average | 97.2 | 79.9 | 69.5 | 68.0 | 66.0 |
| 1% Secant Modulus, MD Std Dev | 3.2 | 1.7 | 0.8 | 6.7 | 3.0 |
| 1% Secant Modulus, CD Average | 101.4 | 83.3 | 66.8 | 72.4 | 76.2 |
| 1% Secant Modulus, CD Std Dev | 2.6 | 1.2 | 2.4 | 1.8 | 5.5 |

The test results of Elmendorf tear properties of the control and experimental multilayer films, which were measured according to ASTM D1922-09, are shown in table 6. The experimental multilayer films had Elmendorf tear strength in the machine direction (MD) of at least about 120 grams.

TABLE 6

Elmendorf tear properties per ASTM D-1922

|  | Unit | 886868 | 886869 | 886870 | 886871 | 886872 |
|---|---|---|---|---|---|---|
| Average Elmendorf, MD | g | 200.1 | 140.4 | 140.2 | 136.0 | 153.0 |
| Std Dev Elmendorf, MD | g | 12.3 | 12.4 | 13.4 | 11.0 | 9.4 |
| Average Elmendorf, CD | g | 166.6 | 127.8 | 129.2 | 136.7 | 132.3 |
| Std Dev Elmendorf, CD | g | 8.2 | 6.8 | 3.1 | 6.4 | 5.7 |
| Thickness | microns | 73.7 | 71.1 | 73.7 | 66 | 66 |

In terms of the desirable weight of the ostomy pouch, the experimental multilayer films have about 10% better yield in grams/m² of film at 65 micron thickness due to having a lower theoretical density, which is an advantage by allowing a lower weight for a typical ostomy pouch of similar size. The desirable lower weight of an ostomy pouch provides advantages to the user who carries the ostomy pouch for daily uses with less weight load.

The theoretical density for the typical SARANEX™ 635G film at 65 microns thickness would be 1.07 g/cm³ and have a film yield of 69.28 g/m². For a similar formulation, replacing the CN-745 compound with the ENGAGE™ based compound would give a theoretical density of 0.967 g/cm³ and have a film yield of 62.61 g/m² at 65 microns thickness, which would provide an advantage for the experimental multilayer film at 9.6% yield.

Example 2. Added Ethylene-Vinyl Acetate (EVA) in Outer Layer

This study was designed to find the optimum level of added ethylene-vinyl acetate (EVA) (added as Elvax® 3150, an EVA copolymer resin contains 15 wt % vinyl acetate comonomer) in the outer layer of the multilayer films to obtain a formulation which provided a soft film with less stuffiness with comparable performances as quiet films in noise intensity measurement.

Five multilayer films (film no. 893763, 893764, 893765, 893767, and 893768) were prepared and tested for sensory testing, noise generation testing (noise intensity measurement), tensile properties, and Elmendorf tear properties. The layers of the multilayer film were joined together and contacted each other in the sequence as outer layer, tie layer 1, barrier layer, and tie layer 2 (as glue layer). The layer profiles of the multilayer films are described in table 7. The compositions of the outer layers are described in table 8. The tie layer comprised 70.6 wt % of Evatane 24-03 (a 24% vinyl acetate copolymer), 20 wt % of Elvax® 3150 LG, 4.8 wt % of CN-4420 (a slip/antiblock additive), 1.6 wt % of Ampacet 101830-U (antiblock compound), and 3 wt % of Ampacet 102113 (process aid additive). The barrier layer contains 100 wt % of SARAN™ XUS-32727.00 polymer (PVDC).

TABLE 7

The layer profiles of the multilayer films

| Film No. | 893763 | 893764 | 893765 | 893767 | 893768 |
|---|---|---|---|---|---|
| Outer, layer profile | 55% | 52% | 54% | 50% | 48% |
| Tie-1, layer profile | 5% | 6% | 6% | 6% | 5% |
| Barrier, layer profile | 7% | 6% | 6% | 6% | 6% |
| Tie-2, layer profile | 33% | 36% | 34% | 36% | 41% |

TABLE 8

The compositions of the outer layer of the multilayer films

|  | Film No. | | | | |
|---|---|---|---|---|---|
|  | 893763 wt % | 893764 wt % | 893765 wt % | 893767 wt % | 893768 wt % |
| ENGAGE ™ mixture (ethylene-octene elastomer) | 70 | 80 | 60 | 50 | NA |
| Dry Blend ENGAGE ™ (ethylene-octene elastomer) | NA | NA | NA | NA | 70 |
| Elvax ® 3150 (EVA) | 26 | 16 | 36 | 46 | 26 |
| CN-4420 (slip antiblock, EVA based) | 3 | 3 | 3 | 3 | 3 |
| Ampacet 102113 (process aid additive) | 1 | 1 | 1 | 1 | 1 |

ENGAGE™ mixture is a 50/50 blend of ENGAGE™ 8100 and ENGAGE™ 8200 at the composition of ENGAGE™ 8100 at 39 wt %, ENGAGE™ 8200 at 39 wt %, Elvax® 3150A at 17.55 wt %, talc at 3.2 wt % and epoxidized soybean oil at 1.25 wt %. The dry blend ENGAGE™ mixture and Elvax® 3150 were in a dry blend formulation of ENGAGE™ 8100 at 35 wt %, ENGAGE™ 8200 at 35 wt %, and Elvax® 3150 at 26 wt %.

Film 893763 was a four-layer multilayer film which was co-extruded with a 55% layer profile of an outer layer comprising 70 wt % of the ethylene-octene elastomer (ENGAGE™ mixture, a 50/50 blend of ENGAGE™ 8100 and ENGAGE™ 8200 at the composition of ENGAGE™ 8100 at 39 wt %, ENGAGE™ 8200 at 39 wt %, Elvax® 3150A at 17.55 wt %, talc at 3.2 wt % and epoxidized soybean oil at 1.25 wt %), 26 wt % of Elvax® 3150 (an EVA copolymer resin contains 15% vinyl acetate comonomer), 3 wt % of CN-4420 (a slip antiblock additive), and 1 wt % of Ampacet 102113 (a process aid additive) (table 8).

Film 893764 was a four-layer multilayer film which was co-extruded with a 52% layer profile of an outer layer comprising 80 wt % of the ethylene-octene elastomer (EN- GAGE™ mixture, a 50/50 blend of ENGAGE™ 8100 and ENGAGE™ 8200 at the composition of ENGAGE™ 8100 at 39 wt %, ENGAGE™ 8200 at 39 wt %, Elvax® 3150A at 17.55 wt %, talc at 3.2 wt % and epoxidized soybean oil at 1.25 wt %), 16 wt % of Elvax® 3150 (an EVA copolymer resin contains 15% vinyl acetate comonomer), 3 wt % of CN-4420 (a slip antiblock additive), and 1 wt % of Ampacet 102113 (a process aid additive) (table 8).

Film 893765 was a four-layer multilayer film which was co-extruded with a 54% layer profile of an outer layer comprising 60 wt % of the ethylene-octene elastomer (ENGAGE™ mixture, a 50/50 blend of ENGAGE™ 8100 and ENGAGE™ 8200 at the composition of ENGAGE™ 8100 at 39 wt %, ENGAGE™ 8200 at 39 wt %, Elvax® 3150A at 17.55 wt %, talc at 3.2 wt % and epoxidized soybean oil at 1.25 wt %), 36 wt % of Elvax® 3150 (an EVA copolymer resin contains 15% vinyl acetate comonomer), 3 wt % of CN-4420 (a slip antiblock additive), and 1 wt % of Ampacet 102113 (a process aid additive) (table 8).

Film 893767 was a four-layer multilayer film which was co-extruded with a 50% layer profile of an outer layer comprising 50 wt % of the ethylene-octene elastomer (ENGAGE™ mixture, a 50/50 blend of ENGAGE™ 8100 and ENGAGE™ 8200 at the composition of ENGAGE™ 8100 at 39 wt %, ENGAGE™ 8200 at 39 wt %, Elvax® 3150A at 17.55 wt %, talc at 3.2 wt % and epoxidized soybean oil at 1.25 wt %), 46 wt % of Elvax® 3150 (an EVA copolymer resin contains 15% vinyl acetate comonomer), 3 wt % of CN-4420 (a slip antiblock additive), and 1 wt % of Ampacet 102113 (a process aid additive) (table 8).

Film 893768 was a four-layer multilayer film which was co-extruded with a 48% layer profile of an outer layer comprising 70 wt % of the ethylene-octene elastomer (dry blend ENGAGE™ mixture), 26 wt % of Elvax® 3150 (an EVA copolymer resin contains 15% vinyl acetate comonomer), 3 wt % of CN-4420 (a slip antiblock additive), and 1 wt % of Ampacet 102113 (a process aid additive) (table 8). The dry blend ENGAGE™ mixture and Elvax® 3150 were in a dry blend formulation of ENGAGE™ 8100 at 35 wt %, ENGAGE™ 8200 at 35 wt %, and Elvax® 3150 at 26 wt %.

Figure 4:
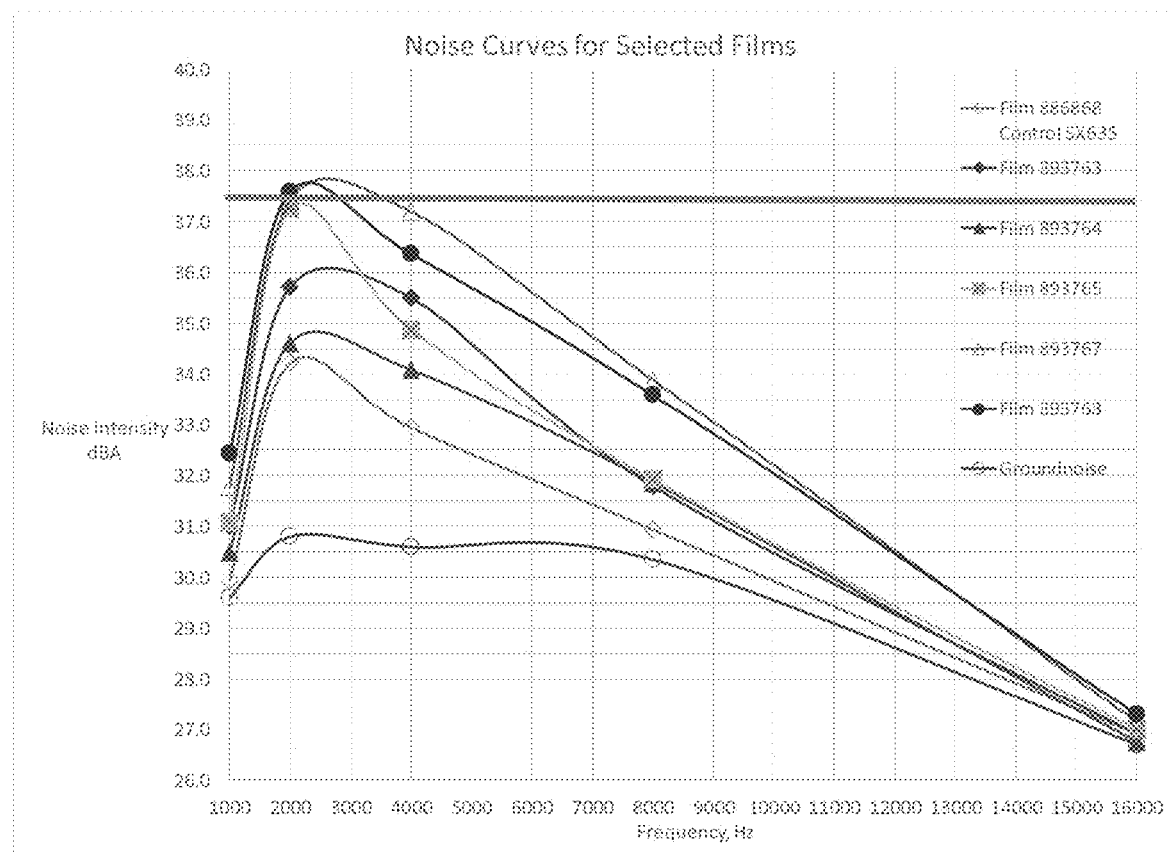
FIG. 4 is a diagram showing noise curves of multilayer films.

The control (film no. 886868) and experimental multilayer films (film no. 893763, 893764, 893765, 893767, and 893768) were tested for noise generation, e.g. noise intensity measurement. All of the experimental multilayer films (film no. 893763, 893764, 893765, 893767, and 893768) had comparable performances as quiet films in the tests of noise generation compared to the control multilayer film (film no. 886868). For noise intensity measurement, the differences of about 3 to 5 dBA or less are not detectable by human ear. As shown in table 9 and FIG. 4, none of the average values of the noise intensities of the experimental multilayer films in the range of 1000 to 16000 Hz showed differences compared to the control multilayer film by more than about 2.5 dBA.

TABLE 9

Noise intensity in dBA for different octave frequency bands

| Film No. | 1 kHz | 2 kHz | 4 kHz | 8 kHz | 16 kHz | Average dBA | Std Dev dBA |
|---|---|---|---|---|---|---|---|
| 886868 | 29.9 | 34.2 | 32.9 | 30.9 | 26.9 | 31.0 | 2.8 |
| 893763 | 31.0 | 35.7 | 35.5 | 31.8 | 26.9 | 32.2 | 3.6 |
| 893764 | 30.5 | 34.6 | 34.1 | 31.9 | 26.8 | 31.6 | 3.2 |
| 893765 | 31.1 | 37.2 | 34.9 | 31.9 | 27.0 | 32.4 | 3.9 |
| 893767 | 31.8 | 37.4 | 37.2 | 33.9 | 27.2 | 33.5 | 4.3 |
| 893768 | 32.4 | 37.6 | 36.4 | 33.6 | 27.3 | 33.5 | 4.0 |
| Ground noise | 29.6 | 30.8 | 30.6 | 30.4 | 26.7 | 29.6 | 1.7 |

Figure 5:
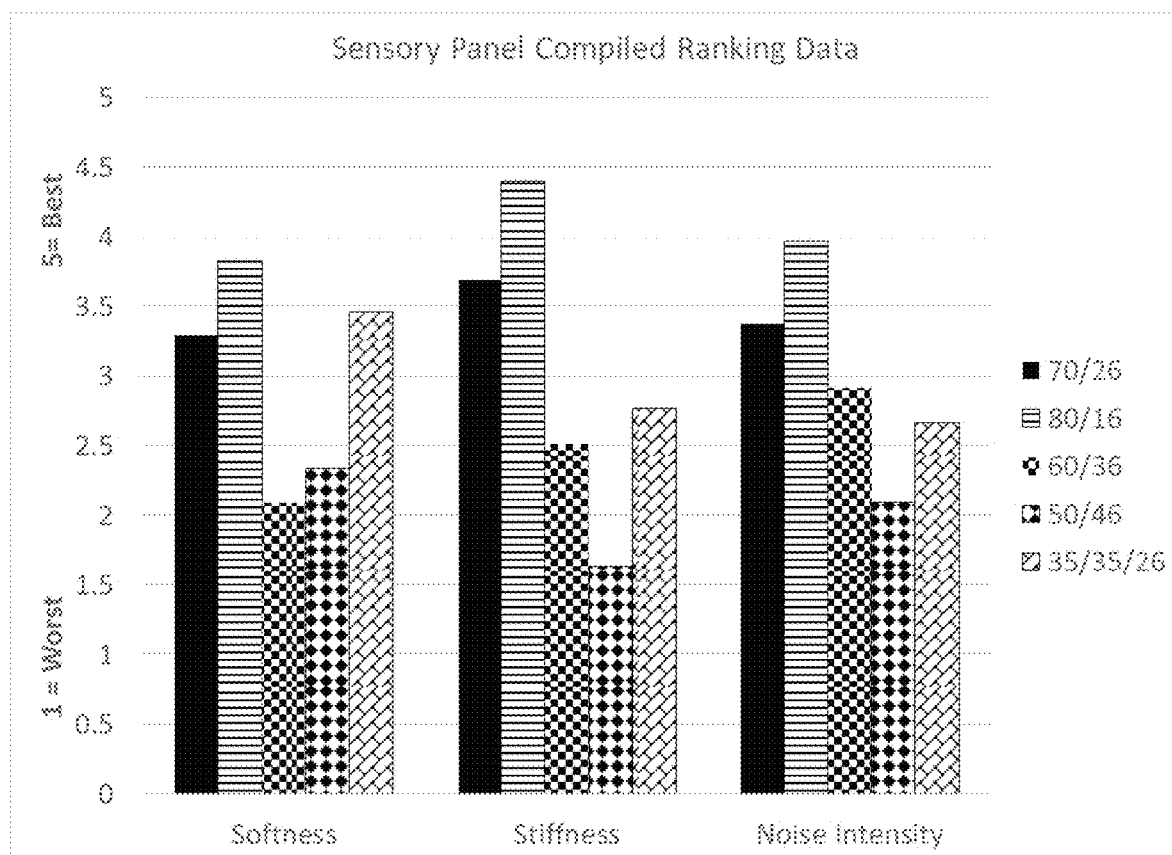
FIG. 5 is a diagram showing the testing results of a sensory panel study which was conducted to evaluate the perception of the haptic characteristics of different multilayer films by ranking the attributes of softness, stiffness and noise intensity in the scale of 1-5. The scale of 5 is defined as "soft", "pliable", or "quiet" for each attribute respectively. The "70/26" multilayer film was film no. 893763; the "80/16" multilayer film was film no. 893764; the "60/36" multilayer film was film no. 893765; the "50/46" multilayer film was film no. 893767; the "35/35/26" multilayer film was film no. 893768.

A sensory panel study with panelists was conducted to evaluate the perception of the haptic characteristics of different multilayer films (five experimental multilayer films; film no. 893763, 893764, 893765, 893767, and 893768) by ranking the attributes of softness, stiffness and noise intensity in the scale of 1-5. The scale of 5 is defined as "soft", "pliable", or "quiet". As shown in FIG. 5, two of the experimental multilayer films (film no. 893763 and 893764) had good performances in ranking the attributes of softness, stiffness and noise intensity as being soft, pliable, and quiet among the five experimental films.

The test results of tensile properties and Secant Modulus of five experimental multilayer films (film no. 893763, 893764, 893765, 893767, and 893768), which were measured according to ASTM D-882, are shown in tables 10 and 11.

TABLE 10

Tensile properties per ASTM D-882

| | 893763 | 893764 | 893765 | 893767 | 893768 |
|---|---|---|---|---|---|
| Thickness, MD (μm) Average | 63.0 | 64.4 | 69.6 | 70.7 | 70.2 |
| Thickness, MD (μm) Std Dev | 1.3 | 1.8 | 2.2 | 2.6 | 2.0 |
| Stress at break, MD (MPa) Average | 21.2 | 22.3 | 21.3 | 20.7 | 21.3 |
| Stress at break, MD (MPa) Std Dev | 1.0 | 0.9 | 0.7 | 0.7 | 0.5 |
| Strain at break, MD (%) Average | 251 | 255 | 263 | 249 | 306 |
| Strain at break, MD (%) Std Dev | 11 | 11 | 7 | 9 | 12 |
| Toughness, MD (MPa) Average | 33.1 | 35.9 | 35.4 | 33.8 | 36.8 |
| Toughness, MD (MPa) Std Dev | 2.5 | 2.1 | 1.9 | 1.4 | 1.6 |
| Stress at break, CD (MPa) Average | 11.6 | 12.8 | 12.2 | 12.7 | 11.7 |
| Stress at break, CD (MPa) Std Dev | 0.3 | 0.6 | 0.4 | 0.4 | 0.2 |
| Strain at break, CD (%) Average | 613 | 641 | 596 | 591 | 549 |
| Strain at break, CD (%) Std Dev | 25 | 21 | 29 | 24 | 18 |
| Toughness, CD (MPa) Average | 35.6 | 40.2 | 36.1 | 37.2 | 30.8 |
| Toughness, CD (MPA) Std Dev | 2.9 | 2.8 | 3.4 | 2.9 | 2.5 |

TABLE 11

Secant Modulus per ASTM D-882 (in MPa)

| | 893763 | 893764 | 893765 | 893767 | 893768 |
|---|---|---|---|---|---|
| 1% Secant Modulus, MD Average | 93.7 | 86.7 | 95.9 | 96.7 | 85.4 |
| 1% Secant Modulus, MD Std Dev | 8.8 | 3.8 | 9.4 | 6.6 | 5.2 |
| 1% Secant Modulus, CD Average | 80.6 | 80.0 | 87.4 | 90.4 | 94.0 |
| 1% Secant Modulus, CD Std Dev | 2.7 | 4.0 | 4.8 | 5.6 | 3.8 |

The test results of Elmendorf tear properties of five experimental multilayer films (film no. 893763, 893764, 893765, 893767, and 893768), which were measured according to ASTM D1922-09, are shown in table 12.

TABLE 12

Elmendorf tear properties per ASTM D-1922

| | Unit | 893763 | 893764 | 893765 | 893767 | 893768 |
|---|---|---|---|---|---|---|
| Average Elmendorf, MD | g | 822.4 | 855.9 | 839.5 | 864.7 | 797.0 |
| Std Dev Elmendorf, MDs | g | 64.8 | 79.5 | 54.8 | 60.4 | 65.5 |
| Average Elmendorf, CD | g | 465.2 | 425.3 | 430.9 | 423.1 | 355.4 |
| Std Dev Elmendorf, CD | g | 18.3 | 15.1 | 22.9 | 37.0 | 24.9 |
| Thickness | Microns | 64.8 | 63.2 | 68.3 | 71.6 | 71.4 |

The results of the above tests showed that added EVA at the level of less than 36 wt % of Elvax® 3150 (an EVA copolymer resin contains 15% vinyl acetate comonomer) in the outer layer formulation had best performances. In addition, the performance of the multilayer with outer layer containing dry blend of ENGAGE™ and Elvax® 3150 (film no. 893768) was not better compared to the pre-compounded version.

It is to be understood that the present application is not to be limited to the exact description and embodiments as illustrated and described herein. To those of ordinary skill in the art, one or more variations and modifications will be understood to be contemplated from the present disclosure. Accordingly, all expedient modifications readily attainable by one of ordinary skill in the art from the disclosure set forth herein, or by routine experimentation therefrom, are deemed to be within the true spirit and scope of the present application as defined by the appended claims.

It would be understood that the various sizes, materials, configurations and arrangements disclosed herein may be combined and constructed in any way that is feasible to create a hybrid for any particular end use. Accordingly, all suitable modifications and equivalents may be resorted to falling within the scope of the appended claims. Unless defined otherwise, all technical and scientific terms used herein have same meaning as commonly understood by one of ordinary skill in the art to which this application belongs. Also, as used herein and in the appended claims, the singular form "a", "and", and "the" include plural referents unless the context clearly dictates otherwise.

What is claimed is:

1. A multilayer film designed for use in ostomy applications, comprising:
an outer layer as a surface protective layer, the outer layer made of a polymer comprising a polyolefin elastomer, a plasticizer of an epoxidized vegetable oil, and a mineral filler;
and a barrier layer; wherein the layers of the film are joined together by an adhesive, wherein the adhesive is provided in a first tie layer that contacts and joins the barrier layer and the outer layer together, and wherein the tie layer is made of a tie layer mixture, wherein the tie layer mixture comprises from 50 wt % to 90 wt % (in the weight of the tie layer mixture) of a first vinyl acetate copolymer, from 10 wt % to 50 wt % (in the weight of the tie layer mixture) of a second vinyl acetate copolymer, and from 5 wt % to 15 wt % (in the weight of the tie layer mixture) of a composition comprising slips, antiblocks and process aids, wherein the vinyl acetate copolymers, slips, antiblocks, process aids, and other additional components are present in a total amount of 100% of the tie layer mixture.

2. The multilayer film of claim 1, wherein the barrier layer is made of a polymer comprisinga polyvinylidene chloride (PVDC) that is plasticized by an epoxidized vegetable oil.

3. The multilayer film of claim 1, wherein the outer layer further comprising an ethylene-vinyl acetate (EVA) copolymer.

4. The multilayer film of claim 1, wherein the outer layer is made of an outer layer mixture, wherein the polyolefin elastomer is in the range of from 20 wt % to 90 wt % of the outer layer mixture, the epoxidized vegetable oil is in the range of from 0.5 wt % to 6.0 wt % ofthe outer layer mixture, and the mineral filler is in the range of from 0.5 wt % to 6 wt % ofthe outer layer mixture, wherein the polyolefin elastomer, the epoxidized vegetable oil, the mineral filler, and other additional components present in a total amount of 100% of the outer layer mixture.

5. The multilayer film of claim 1, wherein the outer layer is made of an outer layer mixture, wherein the outer layer further comprises a slip/antiblock composition in the range of from 1 wt % to 6 wt % of the outer layer mixture.

6. The multilayer film of claim 1, wherein the outer layer further comprises a process aidcomposition.

7. The multilayer film of claim 1, wherein the polyolefin elastomer is an ethylene-octene elastomer.

8. The multilayer film of claim 1, wherein the first vinyl acetate copolymer is a 24% random copolymer, wherein the second vinyl acetate copolymer is a 18% copolymer.

9. The multilayer film of claim 1, wherein a total thickness of the multilayer film is from 45 microns to 85 microns.

10. The multilayer film of claim 1, further comprising first and second enhanced-polymer layers which each comprises a polyethylene polymer, wherein the barrier layer is locatedbetween the first enhanced-polymer layer and the second enhanced-polymer layer.

11. The multilayer film of claim 10, wherein the polyethylene polymer comprises a linear low density polyethylene polymer.

12. The multilayer film of claim 10, wherein the multilayer film comprises seven layers which are next to each other in the sequence of that a first layer is the outer layer, a second layer is the first tie layer, a third layer is the first enhanced-polymer layer, a fourthlayer is the barrier layer, a fifth layer is the second enhanced-polymer layer, a sixth layer is the second tie layer, and the seventh layer is an outer layer.

13. The multilayer film of claim 1, wherein the multilayer film comprising four layers in thesequence of that a first layer is the outer layer, a second layer is the first tie layer, a third layer is the barrier layer, and a fourth layer is a second tie layer.

14. The multilayer film of claim 1, wherein the multilayer film comprises five layers in the sequence of that a first layer is the outer layer, a second layer is the first tie layer, a thirdlayer is the barrier layer, a fourth layer is the second tie layer, and the fifth layer is the outer layer.

15. A product made of the multilayer film of claim 1, wherein the outer layer is made of an outer layer mixture, wherein the polyolefin elastomer is present in an amount of from 20 wt % to 90 wt % of the outer layer mixture, the epoxidized vegetable oil is an epoxidizedsoybean oil, and the mineral filler is talc; wherein the barrier layer comprises a polymercomprising a polyvinylidene chloride that is plasticized by an epoxidized soybean oil.

16. The product of claim 15 in the form of an ostomy bag.

* * * * *